United States Patent
Rousseau et al.

(10) Patent No.: US 10,605,801 B2
(45) Date of Patent: Mar. 31, 2020

(54) METHOD AND DEVICE FOR DETERMINING THE COAGULATION TIME OF A BLOOD SAMPLE, AND REACTION CUVETTE

(71) Applicant: DIAGNOSTICA STAGO, Asnieres-sur-Siene (FR)

(72) Inventors: Alain Rousseau, Paris (FR); Norbert Brutt, Beurey Bauguay (FR); Bertrand Guyon, Chenove (FR)

(73) Assignee: DIAGNOSTICA STAGO, Asnieres-sur-Seine (FR)

( * ) Notice: Subject to any disclaimer, the term of this patent is extended or adjusted under 35 U.S.C. 154(b) by 172 days.

(21) Appl. No.: 15/535,696

(22) PCT Filed: Dec. 9, 2015

(86) PCT No.: PCT/FR2015/053399
§ 371 (c)(1),
(2) Date: Jun. 13, 2017

(87) PCT Pub. No.: WO2016/097536
PCT Pub. Date: Jun. 23, 2016

(65) Prior Publication Data
US 2017/0370905 A1      Dec. 28, 2017

(30) Foreign Application Priority Data

Dec. 15, 2014   (FR) ..................... 14 62423

(51) Int. Cl.
*G01N 33/49*        (2006.01)
*G01N 11/16*        (2006.01)
(Continued)

(52) U.S. Cl.
CPC ......... *G01N 33/4905* (2013.01); *G01N 11/16* (2013.01); *G01N 21/59* (2013.01);
(Continued)

(58) Field of Classification Search
CPC .... G01N 33/4905; G01N 11/16; G01N 21/59; G01N 2011/008; G01N 2203/0089;
(Continued)

(56) References Cited

U.S. PATENT DOCUMENTS

| 4,918,984 A * | 4/1990 | Martinoli | ............ B01F 11/0082 73/64.43 |
| 6,767,511 B1 * | 7/2004 | Rousseau | ............... G01N 11/16 422/62 |

(Continued)

FOREIGN PATENT DOCUMENTS

| EP | 0325874 A1 | 8/1989 |
| EP | 2508891 A1 | 10/2012 |
| EP | 2775292 A1 | 9/2014 |

OTHER PUBLICATIONS

International Search Report for International Application No. PCT/FR2015/053399.

*Primary Examiner* — Lore R Jarrett
(74) *Attorney, Agent, or Firm* — Cantor Colburn LLP

(57) ABSTRACT

This determination method comprises the steps consisting of providing a reaction vessel (2) containing a blood sample (33) and a ferromagnetic ball (11) placed on a raceway (9) provided in the bottom of the reaction vessel (2), subjecting the ball (11) to a magnetic field so as to move the ball along the raceway (9) in an oscillatory motion, exposing the blood sample to an incident light beam (36), detecting a light beam (38) transmitted through the reaction vessel (2) and coming from the incident light beam (36) in such a way as to provide a measurement signal, carrying out a first processing of the measurement signal in such a way as to provide a first signal representative of the variation of at least one physical quantity representative of the movement of the ball (11), carrying out a second processing of the measurement signal in such a way as to provide a second signal representative of (Continued)

the variation of at least one optical property of the blood sample, determining a first value of the coagulation time of the blood sample from the first signal, and determining a second value of the coagulation time of the blood sample from the second signal.

20 Claims, 7 Drawing Sheets

(51) Int. Cl.
  *G01N 21/59* (2006.01)
  *G01N 11/00* (2006.01)
  *G01N 21/82* (2006.01)
(52) U.S. Cl.
  CPC ........ *G01N 21/82* (2013.01); *G01N 2011/008* (2013.01); *G01N 2021/5969* (2013.01); *G01N 2203/0089* (2013.01)

(58) Field of Classification Search
  CPC ........... G01N 2021/5969; G01N 21/82; G01N 33/4915; G01N 33/86; G01N 33/561; G01N 33/49; G01N 27/02; C12Q 1/56
  See application file for complete search history.

(56) References Cited

U.S. PATENT DOCUMENTS

| | | | |
|---|---|---|---|
| 7,507,377 B2* | 3/2009 | Rousseau | G01N 35/026 422/534 |
| 7,943,100 B2* | 5/2011 | Rousseau | B01L 3/50855 422/401 |
| 2009/0117005 A1* | 5/2009 | Rousseau | B01L 3/50855 422/64 |
| 2011/0224292 A1 | 9/2011 | Carroll et al. | |

* cited by examiner

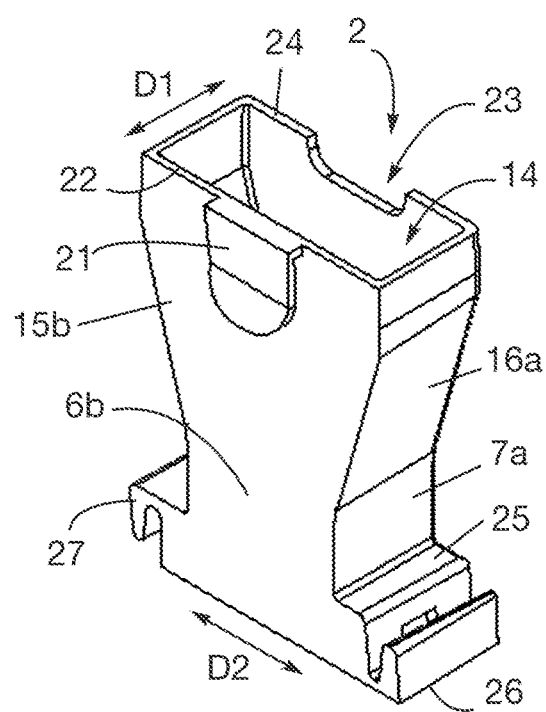
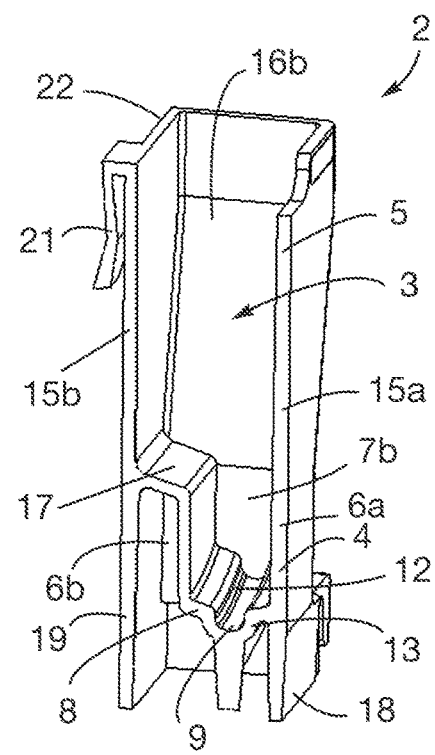
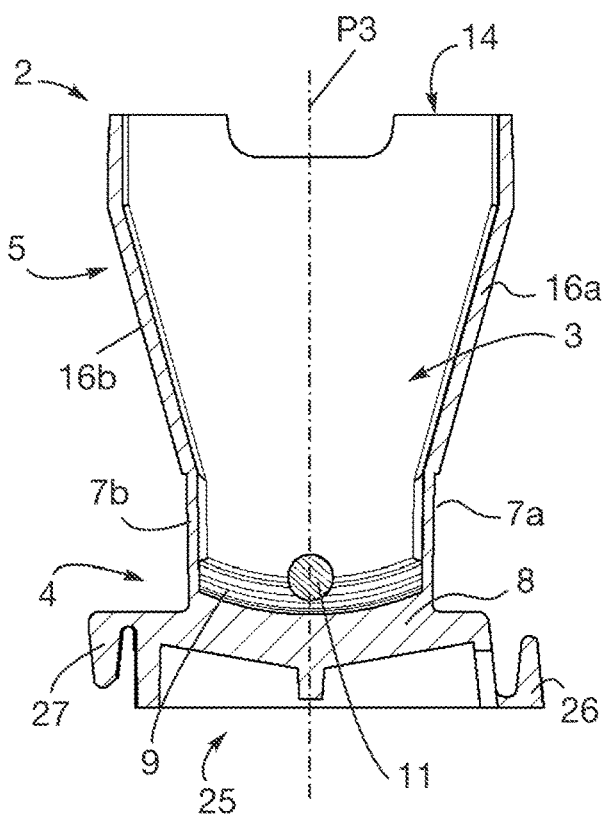
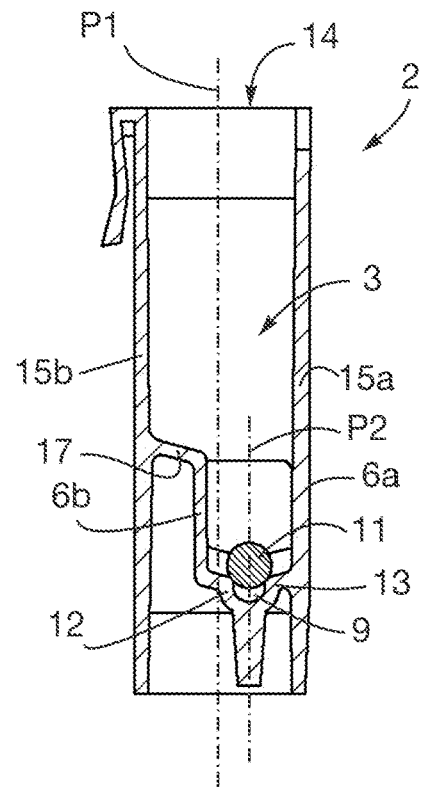
Fig. 1
Fig. 2
Fig. 3
Fig. 4

METHOD AND DEVICE FOR DETERMINING THE COAGULATION TIME OF A BLOOD SAMPLE, AND REACTION CUVETTE

CROSS REFERENCE TO RELATED APPLICATIONS

This application is a National Stage of PCT Application No. PCT/FR2015/053399 filed on Dec. 9, 2015, which claims priority to French Patent Application No. 14/62423 filed on Dec. 15, 2014, the contents each of which are incorporated herein by reference thereto.

TECHNICAL FIELD

The present invention concerns a method and a device for determining the coagulation time of a blood sample to be analyzed, and a reaction cuvette.

BACKGROUND

The document EP 0 325 874 discloses a reaction cuvette allowing determining the coagulation time of a blood sample to be analyzed. To this end, the bottom of the reaction cuvette comprises a curvilinear raceway whose concavity is directed upwards, on which a ferromagnetic ball may be placed and driven in movement.

The document EP 0 325 874 further discloses a method for determining the coagulation time, comprising the following steps:

introducing the blood sample to be analyzed into the reaction cuvette,
placing a ferromagnetic ball on the raceway of the reaction cuvette,
subjecting the ferromagnetic ball to a magnetic field so as to displace the ferromagnetic ball along the raceway in an oscillatory movement,
exposing the blood sample to be analyzed to an incident light beam configured to be substantially tangent to the ferromagnetic ball when it is at the lowest point of the raceway,
detecting at least one light beam transmitted through the reaction cuvette and coming from the incident light beam so as to provide a measurement signal representative of the variation of the amplitude and/or the frequency of the movement of the ferromagnetic ball, and
determining the coagulation time of the blood sample to be analyzed from the measurement signal.

However, when the variation of the amplitude and/or the frequency of the ferromagnetic ball movement is not due to an increase in the viscosity of the blood sample to be analyzed, but on the contrary to the presence of air bubbles and/or impurities in the blood sample, the coagulation time determined by such a determination method is then incorrect, which undermines the reliability of such a determination method.

BRIEF SUMMARY

The present invention aims to overcome this drawback.
The technical problem at the basis of the invention comprises in particular in providing a method and a device for determining the coagulation time of a blood sample to be analyzed which allow reliably and economically determining the coagulation time.

To this end, the present invention concerns a method for determining the coagulation time of a blood sample to be analyzed, comprising the following steps:

providing a reaction cuvette containing the blood sample to be analyzed, the reaction cuvette comprising a bottom delimiting a concave raceway whose concavity is directed upwards,
placing a ferromagnetic ball on the raceway of the reaction cuvette,
subjecting the ferromagnetic ball to a magnetic field so as to displace the ferromagnetic ball along the raceway in an oscillatory movement,
exposing the blood sample to be analyzed to an incident light beam configured to be at least partially obscured by the ferromagnetic ball during at least one part of the oscillatory movement thereof along the raceway,
detecting at least one light beam transmitted through the reaction cuvette and coming from the incident light beam so as to provide a measurement signal,
carrying out a first processing of the measurement signal so as to provide a first signal representative of the variation of at least one physical quantity representative of the movement of the ferromagnetic ball,
carrying out a second processing of the measurement signal so as to provide a second signal representative of the variation of at least one optical property of the blood sample to be analyzed,
determining a first value of the coagulation time of the blood sample to be analyzed from the first signal, and
determining a second value of the coagulation time of the blood sample to be analyzed from the second signal.

Such a determination method allows quantifying the coagulation time according to two different methods, which allows securing the obtained results. Indeed, if the movement of the ferromagnetic ball is prematurely stopped due to the presence, for example, of an air bubble or impurities in the blood sample to be analyzed, the comparison of the first and second determined values allows identifying a difference between the two determined coagulation time values. An operator may then only take into account the second determined value which is less influenced by the stop of the ferromagnetic ball, or else redo the test to ensure a correct measurement of the coagulation time. The determination method according to the present invention thus allows obtaining two independent measurements of the coagulation time, and therefore making the coagulation time measurements reliable.

According to an embodiment of the determination method, the provided measurement signal is obtained by sampling a continuous signal at regular intervals, the duration of an interval preferably being less than 15 ms, for example in the range of 10 ms or 4 ms.

According to an embodiment of the determination method, the first processing of the measurement signal is carried out such that the provided first signal corresponds to the deviation between a high envelope and a low envelope of the measurement signal.

According to another embodiment of the invention, the processing unit is configured such that the provided first signal corresponds to a sliding average of the deviation between the high envelope and the low envelope of the measurement signal, and more precisely a sliding average of the deviation between the high envelope and the low envelope of the measurement signal on a predetermined set of values of the deviation between the high envelope and the low envelope of the measurement signal, for example twelve, corresponding to successive measurement or sampling moments, or over a predetermined sliding interval. Advantageously each value of the first signal for a given measurement or sampling moment is determined as a sliding average of a predetermined set of values of the deviation between the high envelope and the low envelope of the measurement signal $S_M$ corresponding to successive measurement or sampling moments preceding the respective given measurement or sampling moment. Preferably, each value of the first signal for a given measurement or sampling moment is determined as a sliding average of the last values of the deviation between the high envelope and the low envelope of the measurement signal, for example of the last twelve values of the deviation between the high envelope and the low envelope of the measurement signal.

According to an embodiment of the determination method, the high envelope of the measurement signal is determined by connecting the local maximums of the measurement signal, and the low envelope of the measurement signal is determined by connecting the local minimums of the measurement signal.

According to an embodiment of the determination method, the at least one physical quantity representative of the movement of the ferromagnetic ball is the amplitude and/or the frequency of the movement of the ferromagnetic ball.

According to an embodiment of the determination method, the step for determining the first value of the coagulation time of the blood sample to be analyzed comprises a step consisting in providing a base signal corresponding to a sliding average of the first signal, for example over a predetermined sliding interval or on a set of values of the first signal corresponding to successive measurement or sampling moments, the first value of the coagulation time of the blood sample to be analyzed being determined from the base signal.

According to an embodiment of the determination method, each value of the base signal for a given measurement or sampling moment is determined as a sliding average of a set of values of the first signal corresponding to successive measurement or sampling moments comprised in a time interval whose terminals are defined with reference to the given measurement or sampling moment. For example, each value of the base signal for a given measurement or sampling instant is determined as a sliding average of a set of values of the first signal corresponding to measurement or sampling moments comprised in a time interval, advantageously comprised between 8 and 12 seconds and is for example about 10 seconds, preceding the given measurement or sampling moment.

According to another embodiment of the determination method, each value of the base signal for a given measurement or sampling moment is determined as a sliding average of a set of values including the value of the first signal at the respective given measurement or sampling moment and all the values of the first signal corresponding to measurement or sampling moments preceding the respective given measurement or sampling moment.

According to an embodiment of the determination method, the step of determining the first value of the coagulation time of the blood sample to be analyzed comprises a step consisting in determining the intersection point between the first signal and a predetermined percentage of the base signal, the first value of the coagulation time of the blood sample to be analyzed being the time value corresponding to the determined intersection point.

According to an embodiment of the determination method, the predetermined percentage of the base signal is comprised between 30 and 60%.

According to an embodiment of the determination method, the second processing of the measurement signal is carried out such that the provided second signal corresponds to an averaged high envelope of the measurement signal.

According to an embodiment of the determination method, the processing unit is configured such that the provided second signal corresponds to a sliding average of the high envelope of the measurement signal, and more precisely a sliding average of the high envelope of the measurement signal on a predetermined set of values of the high envelope, for example twelve, corresponding to successive measurement or sampling moments, or over a predetermined sliding interval. Advantageously, each value of the second signal for a given measurement or sampling moment is determined as a sliding average of a predetermined set of values of the high envelope corresponding to successive measurement or sampling moments preceding the respective given measurement or sampling moment. Preferably, each value of the second signal for a given measurement or sampling moment is determined as a sliding average of the last values of the high envelope, for example of the last twelve values of the high envelope.

According to an embodiment of the determination method, the step for determining the second value of the coagulation time of the blood sample to be analyzed comprises a step consisting in determining the maximum slope of the second signal, the second value of the coagulation time of the blood sample to be analyzed being the moment corresponding to said maximum slope.

According to an embodiment of the determination method, the latter comprises a step consisting in comparing the determined first and second values of the coagulation time.

According to an embodiment of the determination method, the latter further comprises a step consisting in adjusting the light intensity of the incident light beam depending on an initial value of the measurement signal.

According to an embodiment of the determination method, the reaction cuvette is provided such that the raceway has the lowest point thereof substantially at its center.

According to an embodiment of the determination method, the initial value of the measurement signal corresponds to a position of the ferromagnetic ball substantially at the lowest point of the raceway.

According to an embodiment of the determination method, the latter further comprises a step consisting in adjusting, during an initial phase of the determination method, at least one parameter representative of the magnetic field to which the ferromagnetic ball is subjected depending on the initial values of the measurement signal.

According to an embodiment of the determination method, the at least one parameter representative of the magnetic field to which the ferromagnetic ball is subjected is adjusted depending on the initial values of the first signal.

According to an embodiment of the determination method, the at least one parameter representative of the magnetic field is the period and/or the intensity of the magnetic field to which the ferromagnetic ball is subjected.

According to an embodiment of the determination method, the excitation frequency of the magnetic field is close to the natural frequency of the oscillatory movement of the ferromagnetic ball.

According to an embodiment of the determination method, the magnetic field is generated using a magnetic field generation system transversely shifted relative to the general direction of extension of the raceway. Such an arrangement of the magnetic field generation system allows disposing the emission member vertically in the vicinity of the bottom of the reaction cuvette so as to reduce the distance separating the incident light beam and the bottom of the reaction cuvette, and that without being disturbed by the presence of the magnetic field generation system This also results in a decrease in the amount of reagents and blood sample to be introduced into the reaction cuvette in order to perform each test, and therefore the costs associated with each test.

According to an embodiment of the determination method, the magnetic field generation system is disposed at least partially facing a wall of the reaction cuvette extending substantially parallel to the raceway, and for example facing a longitudinal wall of the reaction cuvette.

According to an embodiment of the determination method, the magnetic field generation system comprises first and second electromagnets disposed respectively in the vicinity of the ends of the raceway. The first and second electromagnets are, for example, disposed on the same side of the raceway.

According to an embodiment of the determination method, the magnetic field may be adjusted by varying, for example, the deviations and/or the length of the electrical pulses applied to the coils of the electromagnets.

According to an embodiment of the determination method, the determination device is configured such that, when the reaction cuvette is received in the receiving housing and the ferromagnetic ball is located at the lowest point of the raceway, the ferromagnetic ball partially obscures the incident light beam.

According to an embodiment of the determination method, the transmitted light beam is detected using a detection member substantially located in the axis of the incident light beam.

According to an embodiment of the determination method, the incident light beam is emitted using an emission member. The emission member and the detection member are, for example, substantially disposed in the axis of the raceway.

The present invention further concerns a device for determining the coagulation time of a blood sample to be analyzed, the determination device comprising:
  a receiving housing in which a reaction cuvette, containing the blood sample to be analyzed and a ferromagnetic ball, is intended to be received, the reaction cuvette delimiting a concave raceway whose concavity is directed upwards and on which the ferromagnetic ball is placed,
  a magnetic field generation system configured to generate a magnetic field capable of displacing the ferromagnetic ball along the raceway in an oscillatory movement when the reaction cuvette is received in the receiving housing,
  an emission member configured to emit an incident light beam in the direction of the blood sample to be analyzed when the reaction cuvette is received in the receiving housing, the incident light beam being configured to be at least partially obscured by the ferromagnetic ball during at least one part of the movement thereof along the raceway,
  a detection member configured to detect at least one light beam transmitted through the reaction cuvette and coming from the incident light beam and to output a measurement signal, and
  a processing unit configured:
  to carry out a first processing of the measurement signal so as to provide a first signal representative of the variation of at least one physical quantity representative of the movement of the ferromagnetic ball,
  to carry out a second processing of the measurement signal so as to provide a second signal representative of the variation of at least one optical property of the blood sample to be analyzed,
  to determine a first value of the coagulation time of the blood sample to be analyzed from the first signal, and
  to determine a second value of the coagulation time of the blood sample to be analyzed from the second signal According to an embodiment of the determination device, the magnetic field generation system is transversely shifted relative to the general direction of extension of the raceway.

According to an embodiment of the invention, the detection member is substantially located in the axis of the incident light beam.

According to an embodiment of the invention, the raceway has the lowest point thereof substantially at its center.

According to an embodiment of the determination device, the ferromagnetic ball and the raceway are configured such that, when the ferromagnetic ball is located at the lowest point of the raceway, the ferromagnetic ball partially obscures the incident light beam.

According to an embodiment of the invention, the obscuration rate of the incident light beam varies between a minimum value corresponding to a position of the ferromagnetic ball at the lowest point of the raceway and a maximum value corresponding to a position of the ferromagnetic ball farthest from the lowest point of the raceway, the minimum value being, for example, comprised between 5 and 10%.

According to an embodiment of the invention, the detection member is a photodetector, such as a photodiode.

According to an embodiment of the invention, the emission member is a light-emitting diode.

According to an embodiment of the invention, the determination device comprises a ferromagnetic ball intended to be placed in the bottom of the reaction cuvette.

According to an embodiment of the invention, the determination device includes a loading system configured to load and unload reaction cuvettes into and out of the reaction housing. The loading system advantageously includes a linear actuator, which may for example comprise an electric stepper motor.

The present invention further concerns a reaction cuvette adapted for implementing the method according to the invention, the reaction cuvette comprising:
  a receptacle configured to contain a biological fluid to be analyzed, the receptacle comprising:
  a lower portion including a bottom delimiting a concave raceway whose concavity is directed upwards, the raceway having the lowest point thereof substantially at its center and being intended to guide an oscillatory movement of a ferromagnetic ball,
  an upper portion delimiting an insertion opening,
  first hooking means configured to hook the reaction cuvette to a first adjacent reaction cuvette in a first hooking direction, and
  second hooking means configured to hook the reaction cuvette to a second adjacent reaction cuvette in a second hooking direction which is substantially perpendicular to the first hooking direction, the reaction cuvette being characterized in that the width of the lower portion of the receptacle transversely to the general direction of extension of the raceway is smaller than the width of the upper portion of the receptacle transversely to the direction of extension of the raceway, and in that the raceway is transversely shifted relative to a median longitudinal plane of the upper portion of the receptacle.

Consequently, the raceway is therefore closer to a first longitudinal wall of the reaction cuvette than to a second longitudinal wall of the reaction cuvette opposite to said first longitudinal wall.

Such a configuration of the reaction cuvette allows performing coagulation time measurements in a reduced reaction volume, for example less than 90 μL, and thus reducing the collected amount of sample and also the amount of used reagents. This results in a significant decrease in the costs associated with each performed test.

Furthermore, in the context of immunological measurements using magnetic particles, such a configuration of the reaction cuvette ensures a positioning of a magnet or electromagnet, during washing operations of the magnetic particles, as close as possible to the reaction area of the reaction cuvette (by placing it substantially in contact with the longitudinal wall of the reaction cuvette the closest to the raceway), and therefore an optimal magnetic attraction of the magnetic particles against a longitudinal wall of the reaction cuvette, which allows avoiding any risk of removal of a portion of the magnetic particles bound to the analyte to be quantified out of the reaction cuvette with the washing solution.

In addition, in the context of immunological measurements using magnetic particles, such a configuration of the reaction cuvette ensures a positioning of an optical reading member as close as possible to the reaction area of the reaction cuvette, and therefore accurate and reliable measurement results.

According to an embodiment of the invention, the upper portion of the receptacle is flared in the direction of the insertion opening.

According to an embodiment of the invention, the lower portion of the receptacle is substantially parallelepiped-shaped and is elongated in the general direction of extension of the raceway.

According to an embodiment of the invention, the first hooking means include at least one hooking tab directed downwards and extending from an upper edge of the upper portion of the receptacle.

According to an embodiment of the invention, the reaction cuvette includes a notch formed on an upper edge of the upper portion of the receptacle opposite to the upper edge from which the hooking tab extends, the hooking tab of a reaction cuvette being intended to cooperate with the notch of an adjacent reaction cuvette in the first hooking direction.

According to an embodiment of the invention, the second hooking means include a first upwardly-open hook and a second downwardly-open hook, the first upwardly-open hook being configured to engage with the second downwardly-open hook at the bottom of an adjacent reaction cuvette, the first and second hooks being provided on a base of the reaction cuvette, along two edges opposite and orthogonal to the upper edge from which the hooking tab extends.

According to an embodiment of the invention, the raceway has the shape of a cylinder portion with a radius comprised between 8 and 10 mm.

BRIEF DESCRIPTION OF THE DRAWINGS

In any case, the invention will be well understood using the following description with reference to the appended schematic drawing representing, by way of non-limiting examples, an embodiment of this determination device and of this reaction cuvette.

FIG. 1 is a perspective view of a reaction cuvette according to the invention.

FIG. 2 is a perspective, cross-sectional view of the reaction cuvette of FIG. 1.

FIG. 3 is a longitudinal sectional view of the reaction cuvette of FIG. 1 equipped with a ferromagnetic ball.

FIG. 4 is a cross-sectional view of the reaction cuvette of FIG. 1 equipped with a ferromagnetic ball.

DETAILED DESCRIPTION

Figure 5:
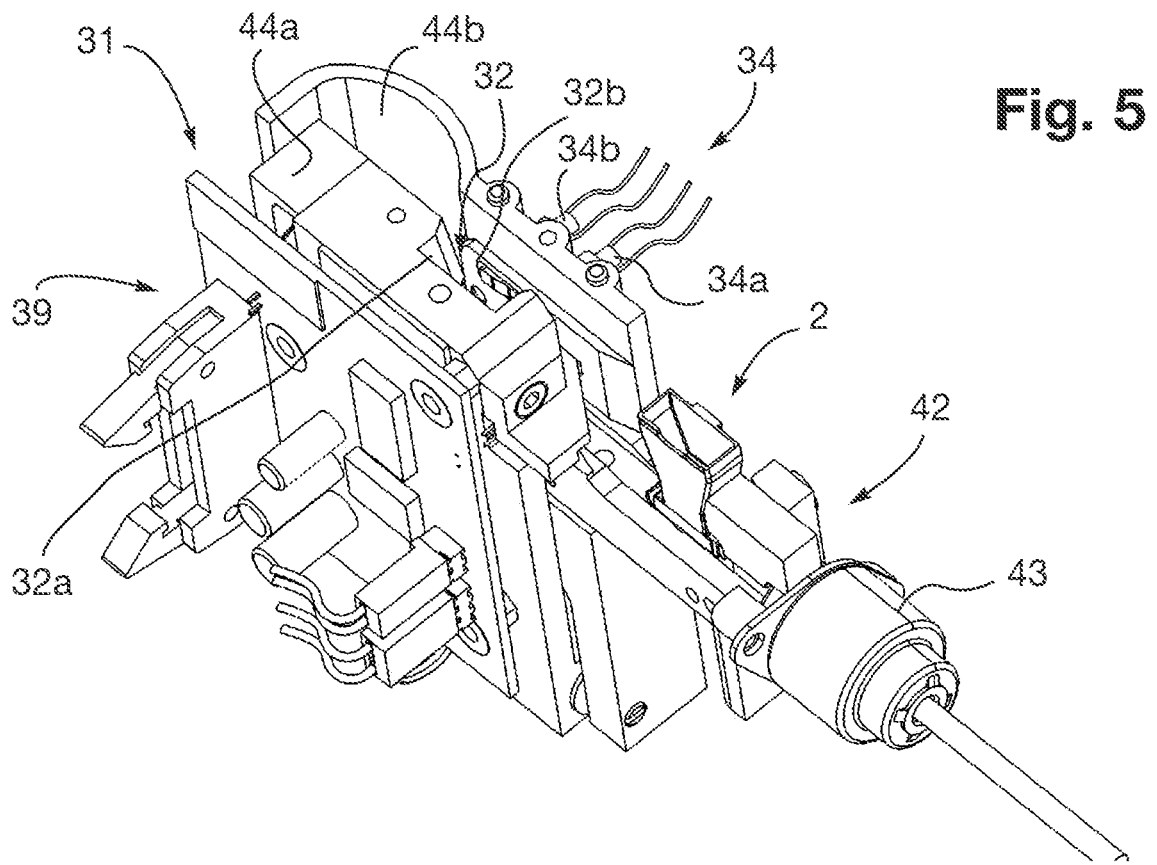
FIGS. 5 to 8 are perspective views of a coagulation time determination device according to the invention equipped with a reaction cuvette and in different operating positions.
Figure 6:
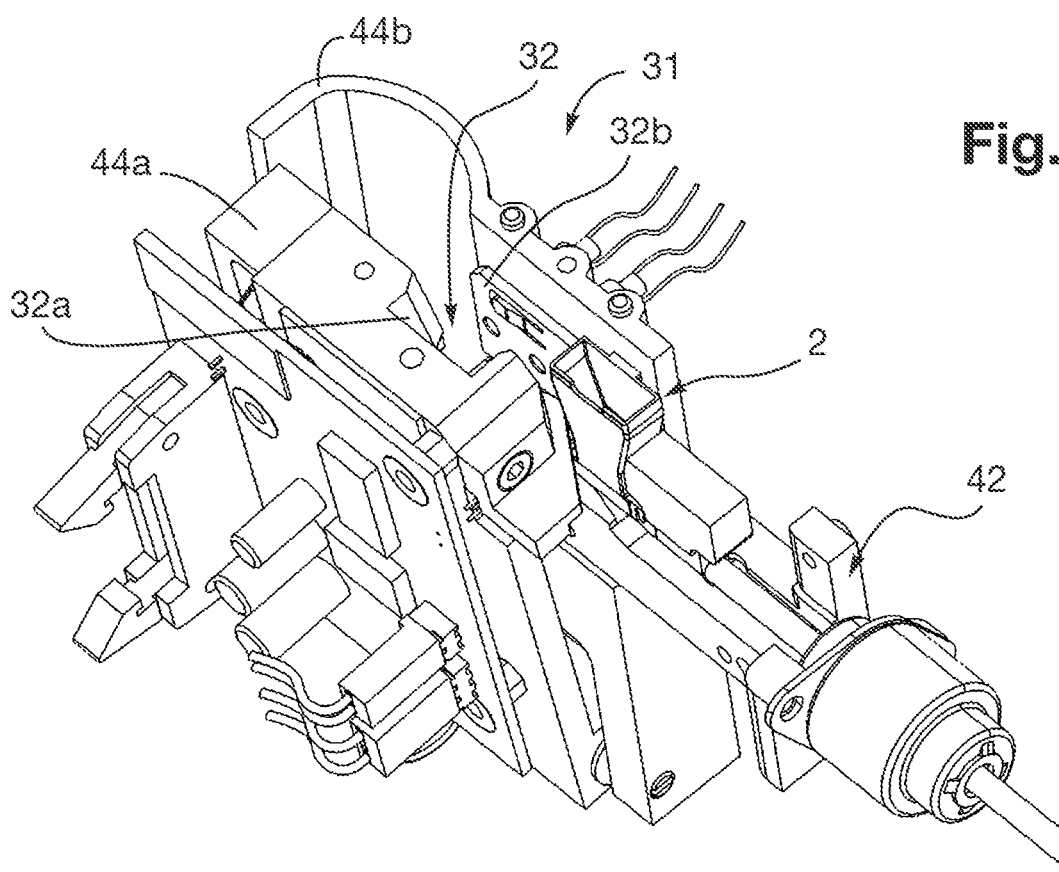
Figure 7:
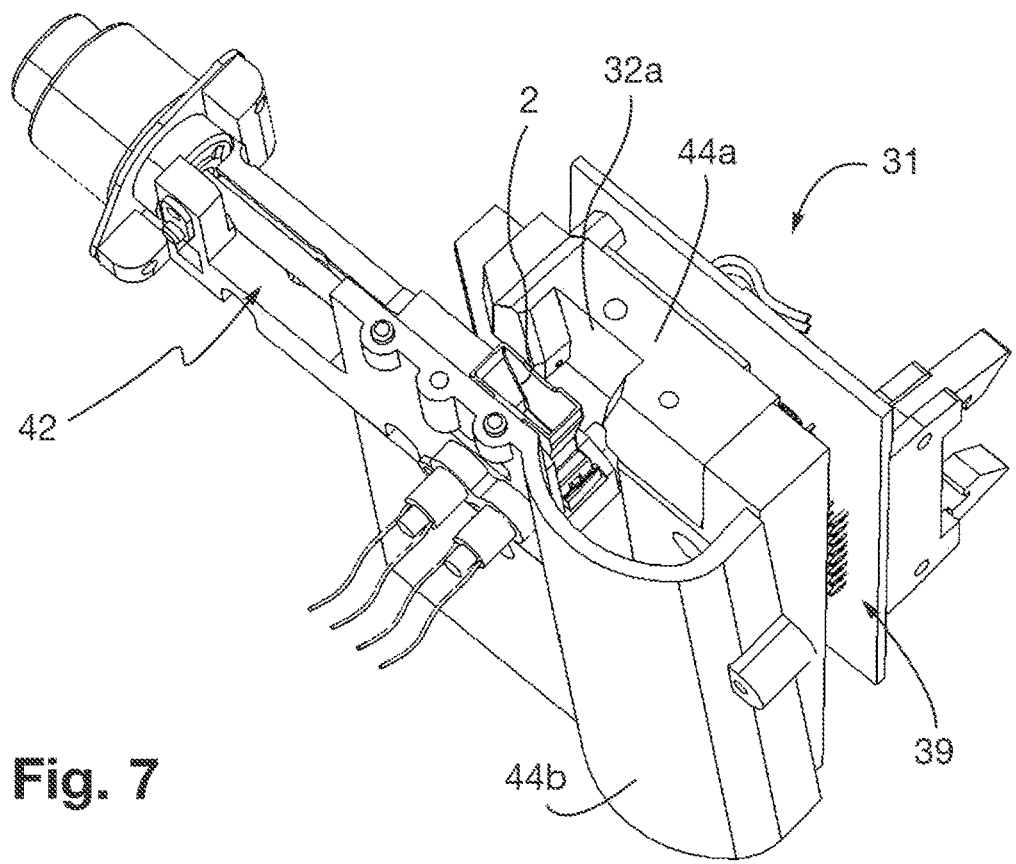
Figure 8:
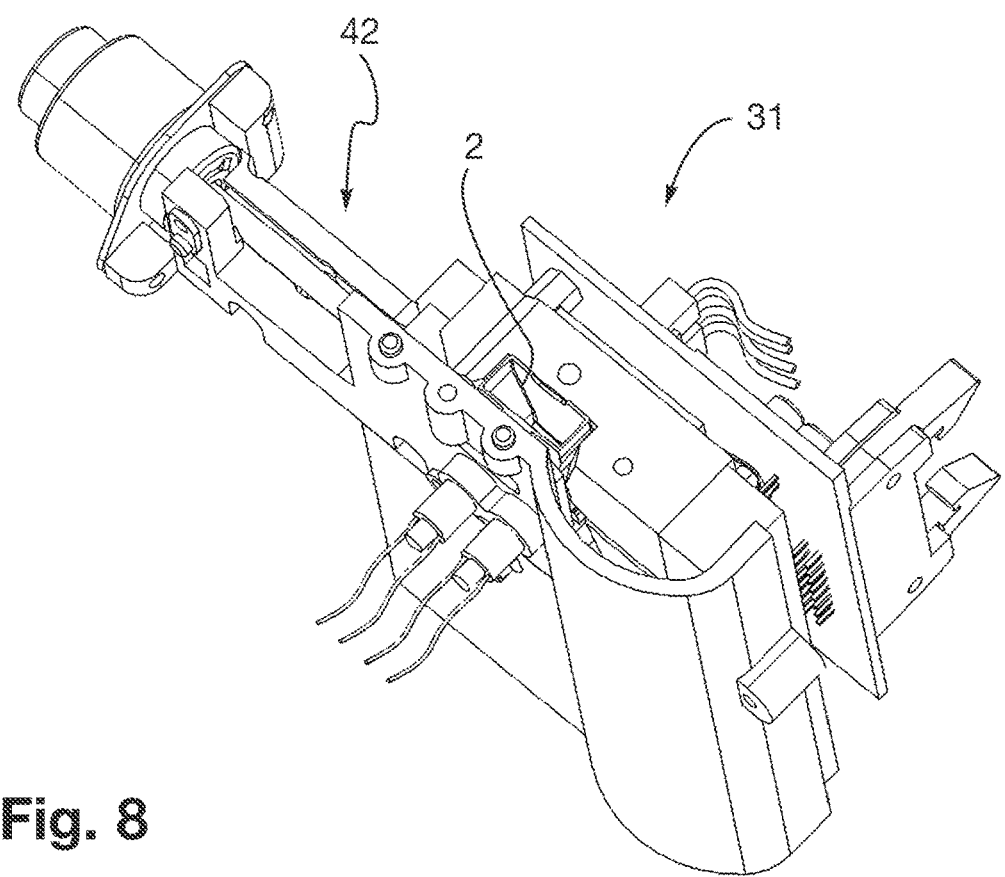
Figure 9:
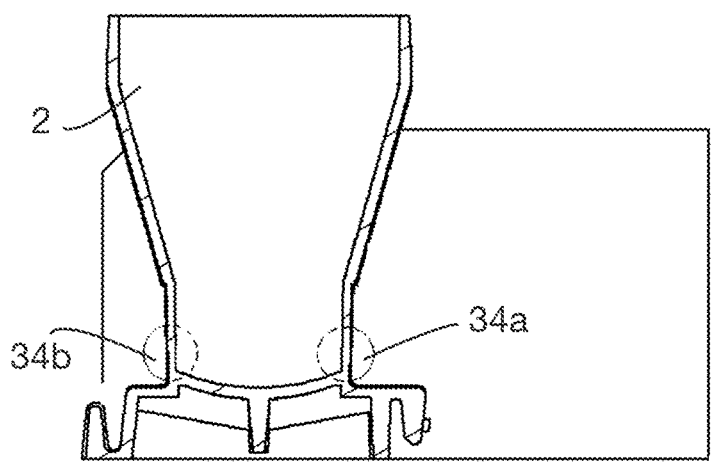
FIG. 9 is a schematic sectional view showing the relative arrangement between a magnetic field generation system of the determination device of FIG. 5 and a reaction cuvette equipping this determination device.

FIGS. 1 to 4 represent a unitary reaction cuvette 2 made of plastic material transparent to the light beams. The reaction cuvette 2 comprises a receptacle 3 configured to contain a biological fluid to be analyzed, such as a blood sample. The receptacle 3 has, for example, a height in the range of 22 mm and may for example contain up to 600 μL of biological fluid to be analyzed.

The receptacle 3 comprises a lower portion 4 and an upper portion 5 extending the lower portion 4. The lower portion 4 is substantially parallelepiped-shaped and has, for example, a length in the range of 8 mm and a width in the range of 3 mm. The lower portion 4 includes two longitudinal walls 6a, 6b, parallel to each other, two transverse walls 7a, 7b parallel to each other and a bottom 8. The bottom 8 delimits a concave raceway 9 whose concavity is directed upwards.

The raceway 9 is elongated in the longitudinal direction of the lower portion 4 of the receptacle 3 and has its lowest point substantially at its center. The raceway 9 is intended to guide an oscillatory movement of a ferromagnetic ball 11. The raceway 9 may be, for example, curvilinear and substantially V-shaped, or as can be seen in FIG. 3, have the shape of a cylinder portion. According to the embodiment represented in the figures, the raceway 9 is delimited by two lateral rails 12, 13 formed in the bottom 8 of the lower portion 4 of the receptacle 3. These two lateral rails 12, 13 allow more particularly guiding the oscillatory movement of the ferromagnetic ball 11 in the reaction cuvette 2.

The upper portion 5 of the receptacle 3 flares opposite the bottom 8 and delimits an insertion opening 14. The upper portion 5 has, for example, a generally truncated-conical shape. The upper portion 5 includes two longitudinal walls 15a, 15b parallel to each other, and two transverse walls 16a, 16b connecting the longitudinal walls 15a, 15b to each other, the longitudinal walls 15a, 15b and the transverse walls 16a, 16b delimiting the insertion opening 14.

According to the embodiment represented in the figures, the upper portion 5 further includes a connecting wall 17 connecting the longitudinal walls 6b, 15b, the connecting wall 17 being inclined with respect to the longitudinal walls 6b, 15b. According to this embodiment of the invention, the longitudinal walls 6a, 15a are coplanar whereas the longitudinal walls 6b, 15b are parallel and shifted relative to each other.

The transverse direction D1 is defined as the direction orthogonal to the longitudinal walls 6a, 6b and the longitudinal direction D2 as the direction orthogonal to the transverse walls 7a, 7b. The plane P1 is also defined as the median longitudinal plane of the upper portion 5 of the receptacle 3, the plane P2 as the median longitudinal plane of the lower portion 4 of the receptacle 3, and the plane P3 as the median transverse plane P3 of the receptacle (see FIGS. 3 and 4).

As can be seen more particularly in FIGS. 2 and 4, the width of the lower portion 4 of the receptacle 3 perpendicularly to the general direction of extension of the raceway 9, that is to say in the direction D1, is smaller than the width of the upper portion 5 of the receptacle 3 perpendicularly to the direction of extension of the raceway 9, that is to say in the direction D1.

Furthermore, the lower portion 4 of the receptacle 3, and more particularly the raceway 9, is transversely shifted relative to the median longitudinal plane P1 of the upper portion 5 of the receptacle 3. Consequently, the raceway 9 is closer to the longitudinal wall 6a of the lower portion 4 than to the longitudinal wall 6b.

According to the embodiment represented in the figures, the reaction cuvette 2 further comprises a first finishing wall 18 extending in the extension of the longitudinal wall 6a opposite the insertion opening 14, and a second finishing wall 19 extending in the extension of the longitudinal wall 15b opposite the insertion opening 14.

The reaction cuvette 2 also comprises a hooking tab 21 directed downwards and extending from an upper longitudinal edge 22 of the upper portion 5 of the receptacle 3. The reaction receptacle 2 further includes a notch 23 formed on an upper longitudinal edge 24 of the upper portion 5 opposite to the upper longitudinal edge 22. The notch 23 has dimensions adapted to those of the hooking tab 21 such that the hooking tab 21 of a reaction cuvette 2 is intended to cooperate with the notch 23 of an adjacent reaction cuvette 2 in the direction D1 in order to hook two adjacent reaction cuvettes 2.

Furthermore, the reaction cuvette 2 includes a base 25 in the lower portion, in which are formed, along two opposite edges parallel to the direction D1, a first overhang 26 forming a first upwardly-open hook and a second overhang 27 forming a second downwardly-open hook. The first upwardly-open hook is configured to engage with the second downwardly-open hook of an adjacent reaction cuvette 2 in the direction D2, In order to hook two adjacent reaction cuvettes 2.

Thanks to the structure of the hooking tab 21 and the first and second overhangs 26 and 27, it is possible to hook reaction cuvettes 2 to each other in two orthogonal directions, manually or automatically, in order to form plates. Furthermore, the overhangs 26, 27 allow having overall dimensions of the reaction cuvettes 2 which are substantially the same in their upper portions 5 and in their lower portions 4 such that when assembled together, the reaction cups 2 constitute a flat plate. This allows arranging the reaction cuvettes 2 in order to store them in a simple, compact manner, while allowing easily detaching a reaction cuvette 2 from the corresponding plate.

FIGS. 5 to 13 represent a determination device 31 configured to determine the coagulation time of a blood sample to be analyzed.

The determination device 31 comprises a receiving housing 32 into which a reaction cuvette 2, containing the blood sample to be analyzed 33 and a ferromagnetic ball 11 placed on the raceway 9, is intended to be received.

The determination device 31 also comprises a magnetic field generation system 34 configured to generate a magnetic field capable of displacing the ferromagnetic ball 11 along the raceway 9 in an oscillatory movement when the reaction cuvette 2 is received in the receiving housing 32. The excitation frequency of the magnetic field generated by the magnetic field generation system 34 is advantageously close to the natural frequency of the oscillatory movement of the ferromagnetic ball 11, and is for example in the range of 3.125 Hz (period in the range of 320 ms).

The determination device 31 is configured such that the magnetic field generation system 34 is transversely shifted relative to the general direction of extension of the raceway 9 when the reaction cuvette 2 is received in the receiving housing 32. More particularly, the determination device 31 is configured such that the magnetic field generation system 34 is disposed at least partially facing a longitudinal wall, for example the longitudinal wall 6b, of the receptacle 3 when the reaction cuvette 2 is received in the receiving housing 32.

The magnetic field generation system 34 advantageously comprises two electromagnets 34a, 34b disposed respectively in the vicinity of the ends of the raceway 9 and at a same side of the raceway 9, when the reaction cuvette 2 is received in the receiving housing 32. The magnetic field generated by the magnetic field generation system 34 may be advantageously adjusted by varying, for example, the deviations and/or the length of the electrical pulses applied to the coils of the electromagnets 34a, 34b.

The determination device 31 further comprises an emission member 35 configured to emit an incident light beam 36 in the direction of the blood sample to be analyzed 33 when the reaction cuvette 2 is received in the receiving housing 32. The emission member 35 may for example be a light-emitting diode.

Figure 10:
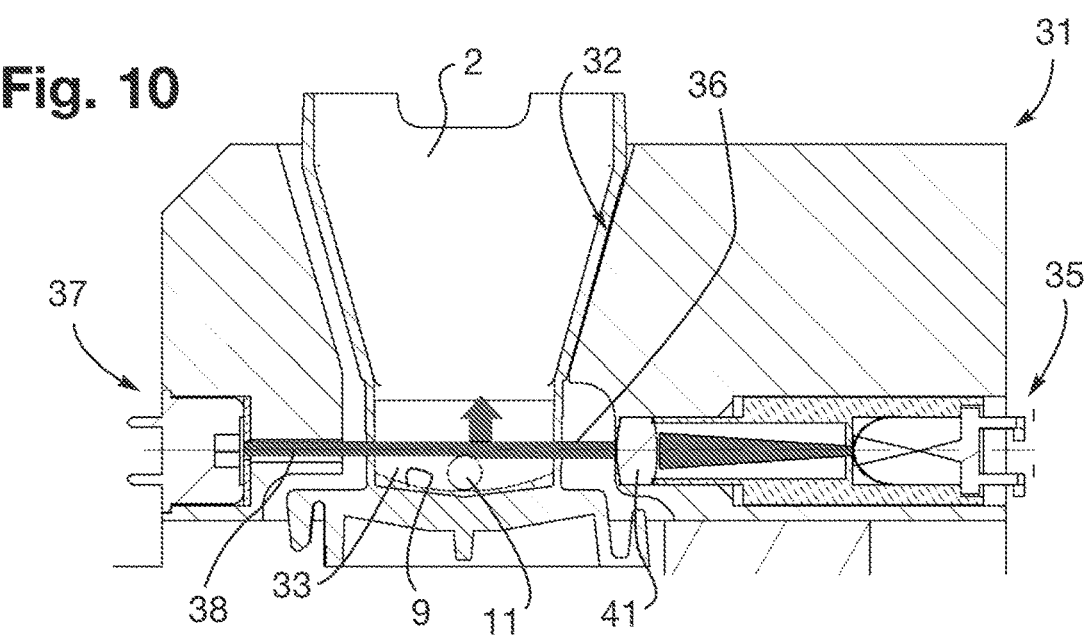
FIGS. 10 to 13 are partial longitudinal sectional views of the determination device of FIG. 5 showing different positions occupied by a ferromagnetic ball placed on a raceway of the reaction cuvette.
Figure 11:
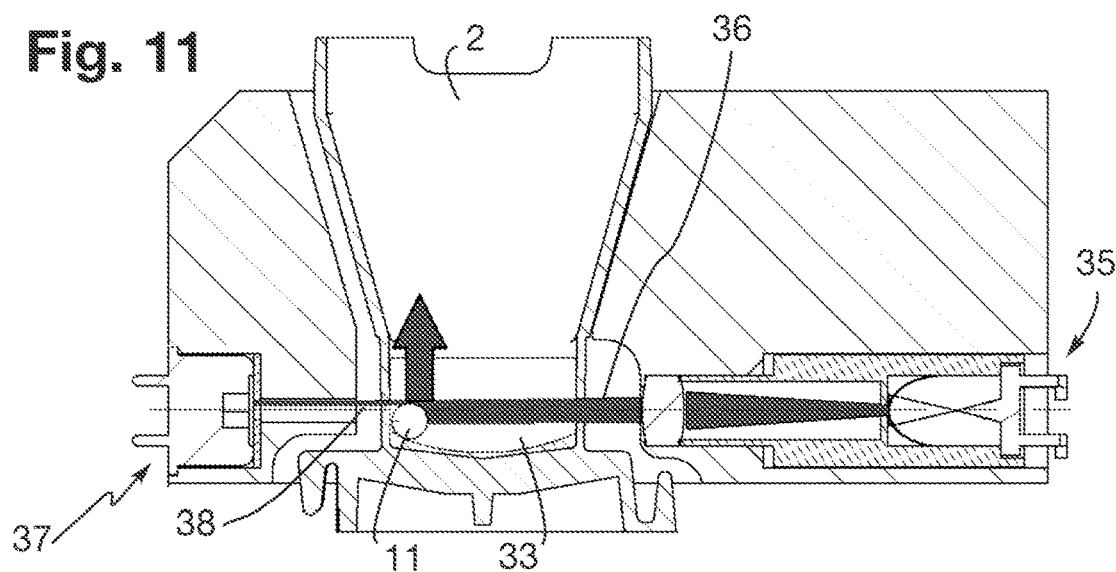
Figure 12:
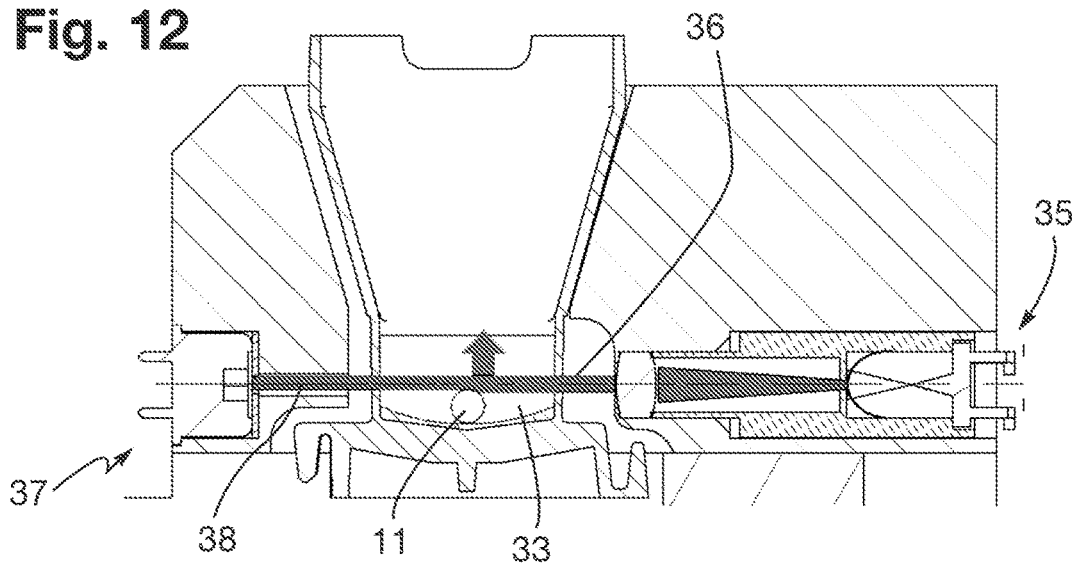
Figure 13:
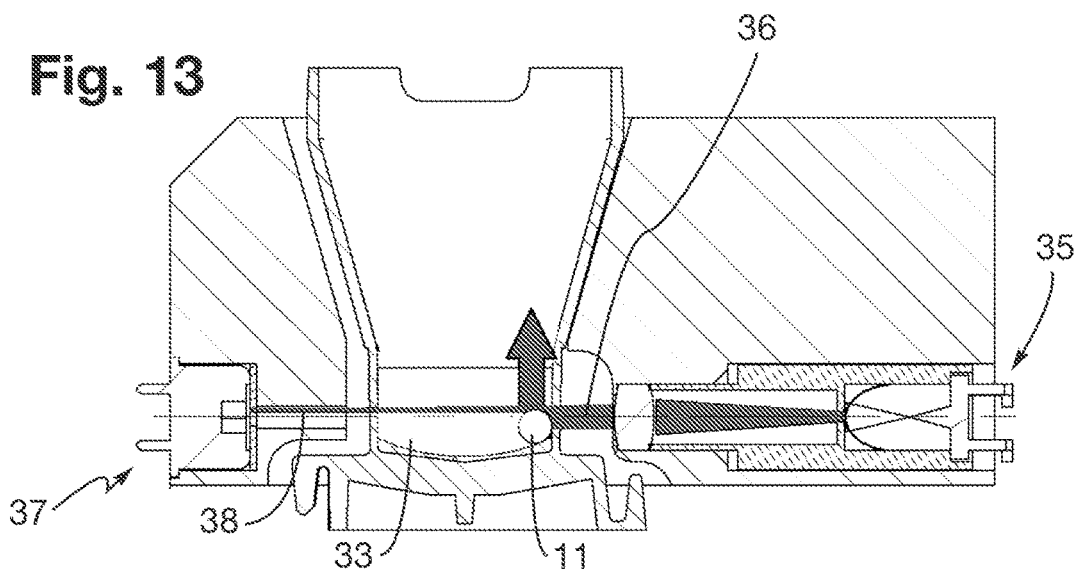

According to the embodiment represented in the figures, the determination device 31 is configured such that, when the reaction cuvette 2 is received in the receiving housing 32 and the ferromagnetic ball 11 is located at the lowest point of the raceway 9, the ferromagnetic ball 11 partially obscures the incident light beam 36 (see FIGS. 10 and 12).

According to an embodiment of the invention, the obscuration rate of the incident light beam 36 varies between a minimum value corresponding to a position of the ferromagnetic ball 11 at the lowest point of the raceway 9 (see FIGS. 10 and 12) and a maximum value corresponding to a position of the ferromagnetic ball 11 farthest from the lowest point of the raceway 9 (see FIGS. 11 and 13), the minimum value being, for example, comprised between 5 and 10%.

Figure 15:
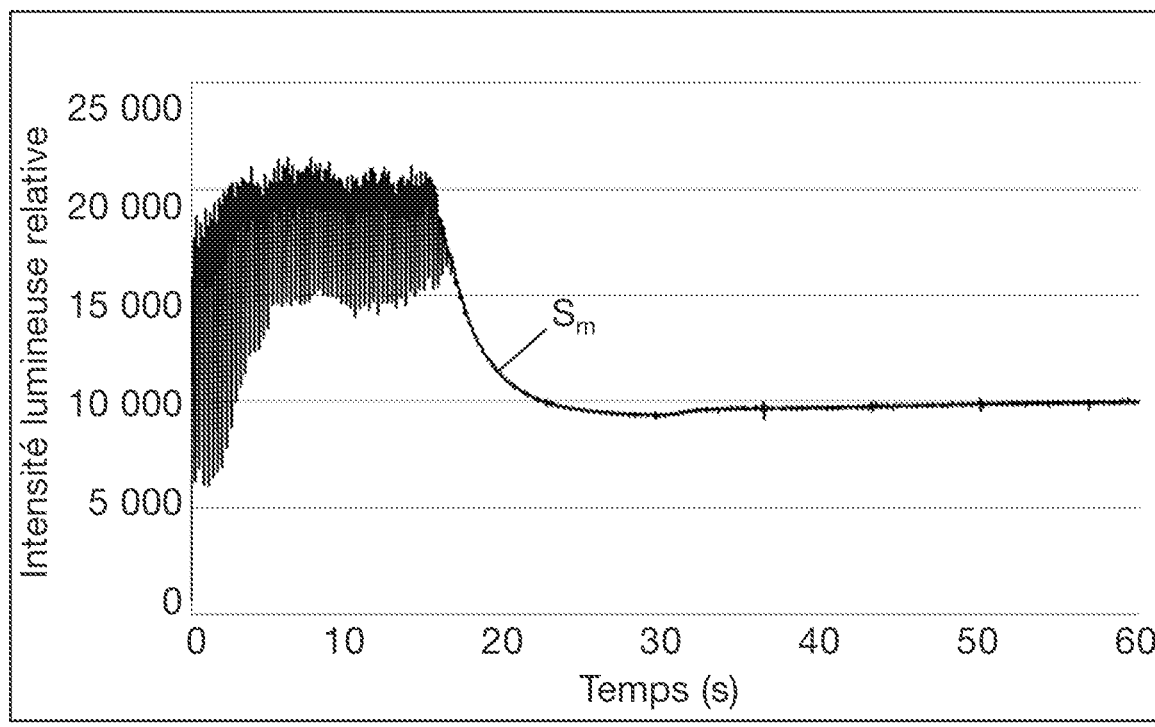
FIG. 15 is a diagram representing the evolution of the amplitude of a measurement signal depending on the time.

The determination device 31 further comprises a detection member 37 configured to detect at least one light beam 38 transmitted through the reaction cuvette 2 and coming from the incident light beam 36, and to output a measurement signal $S_M$. FIG. 15 represents the evolution of the amplitude of an example of a measurement signal $S_M$ depending on the time, and more particularly the evolution of the relative light intensity of an example of measurement signal $S_M$ depending on the time.

The detection member 37 may for example be a photodetector, such as a photodiode. According to the embodiment represented in the figures, the detection member 37 is substantially located in the axis of the incident light beam 36. Thus, according to the embodiment represented in the figures, the emission and detection members are disposed on either side of the ends of the raceway 9 when the reaction cuvette 2 is received in the receiving housing 32.

According to an embodiment of the invention, the measurement signal $S_M$ is obtained by sampling a continuous signal at regular intervals, the duration of an interval, that is to say between two sampling moments, being for example in the range of 10 ms.

The determination device 31 also comprises a processing unit 39. As shown in particular in FIG. 5, the processing unit 39 may be disposed in the vicinity of the receiving housing 32. Nevertheless, the processing unit 39 may also be drifted at a distance from the measurement area.

The processing unit 39 is more particularly configured:
to carry out a first processing of the measurement signal $S_M$ so as to provide a first signal S1 representative of the variation of at least one physical quantity representative of the movement of the ferromagnetic ball 11, the at least one physical quantity representative of the movement of the ferromagnetic ball 11 being, for example, the amplitude and/or the frequency of the movement of the ferromagnetic ball 11,
to carry out a second processing of the measurement signal $S_M$ so as to provide a second signal S2 representative of the variation of at least one optical property of the blood sample to be analyzed 33, the at least one optical property of the blood sample to be analyzed 33 being, for example, the absorbance of the blood sample to be analyzed 33,
to determine a first value t1 of the coagulation time of the blood sample to be analyzed from the first signal S1, and
to determine a second value t2 of the coagulation time of the blood sample to be analyzed from the second signal S2.

Figure 16:
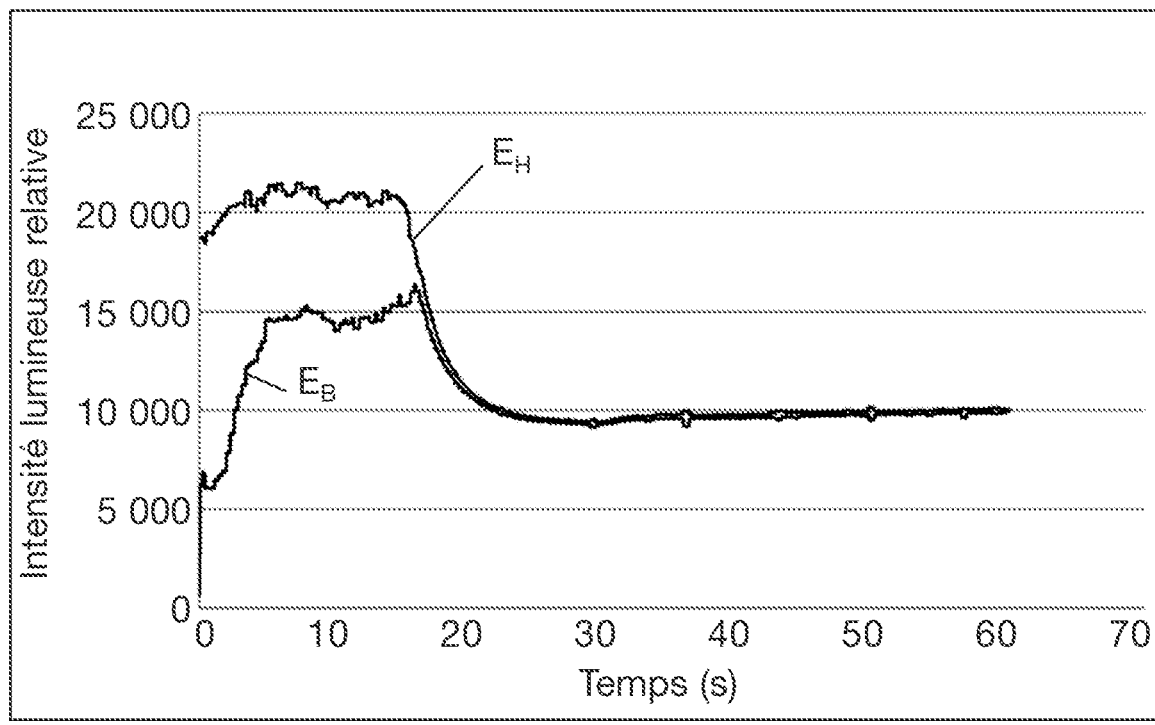
FIG. 16 is a diagram representing the evolution of the amplitude of the low and high envelopes of the measurement signal depending on the time.

According to an embodiment of the invention, the processing unit 39 is configured such that the provided first signal S1 corresponds to the deviation between a high envelope and a low envelope of the measurement signal $S_M$. The high envelope of the measurement signal is determined by connecting the local maximums of the measurement signal $S_M$, whereas the low envelope of the measurement signal is determined by connecting the local minimums of the measurement signal $S_M$. FIG. 16 represents the evolution of the amplitude of the low and high envelopes EB and EH depending on the time, and more particularly the evolution of the relative light intensity of the low and high envelopes EB and EH depending on the time.

According to another embodiment of the invention, the processing unit 39 is configured such that the provided first signal S1 corresponds to a sliding average of the deviation between the high envelope and the low envelope of the measurement signal $S_M$ on a predetermined set of values of the deviation between the high envelope and the low envelope of the measurement signal $S_M$, for example twelve, corresponding to successive measurement or sampling moments. Preferably, each value of the first signal S1 for a given measurement or sampling moment is determined as a sliding average of the last values of the deviation between the high envelope and the low envelope of the measurement signal $S_M$, for example of the last twelve values of the deviation between the high envelope and the low envelope of the measurement signal $S_M$.

According to an embodiment of the invention, the processing unit 39 is configured to provide a base signal corresponding to a sliding average of the first signal S1 over a predetermined sliding interval. More particularly, each value of the base signal for a given measurement or sampling moment is determined as a sliding average of a set of values of the first signal S1 corresponding to measurement or sampling moments comprised in a time interval whose terminals are defined with reference to the given measurement or sampling moment. For example, the time interval is 10 seconds, and precedes, for each value of the base signal, the respective given measurement or sampling moment.

Figure 17:
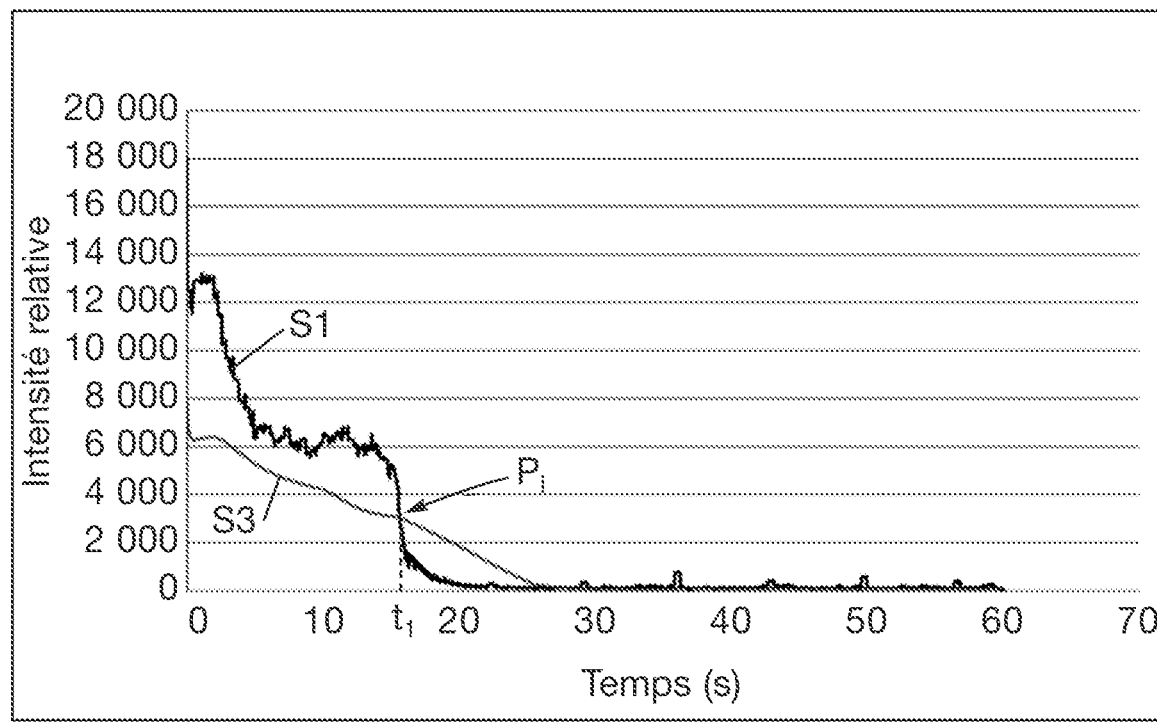
FIG. 17 is a diagram representing the evolution of the deviation between the high and low envelopes of the measurement signal and the evolution of a predetermined percentage of a base signal determined from the deviation between the high and low envelopes of the measurement signal.

According to another embodiment of the determination method, each value of the base signal for a given measurement or sampling moment is determined as a sliding average of a set of values including the value of the first signal S1 at the respective given measurement or sampling moment and all the values of the first signal S1 corresponding to measurement or sampling moments preceding the respective given measurement or sampling moment. According to an embodiment of the invention, the processing unit 39 is configured to determine the intersection point Pi between the first signal S1 and a third signal S3 corresponding to a predetermined percentage of the base signal, the first value t1 of the coagulation time of the blood sample to be analyzed determined by the processing unit 39 then being the moment corresponding to the determined intersection point Pi. According to an embodiment of the invention, the third signal is comprised between 30 and 60% of the base signal. FIG. 17 represents the evolution of the amplitude of the first and third signals S1, S3 depending on the time, and more particularly the evolution of the relative light intensity of the first and third signals S1, S3 depending on the time. It should be noted that the predetermined percentage of the base signal may be programmed depending on the tests to be performed, and for example depending on the reaction volume of the used reaction cuvettes.

According to an embodiment of the invention, the processing unit 39 is configured such that the provided second signal S2 corresponds to an averaged high envelope of the measurement signal $S_M$. For example, the processing unit 39 is configured such that the provided second signal S2 corresponds to a sliding average of the high envelope of the measurement signal on a predetermined set of values of the high envelope, for example twelve, corresponding to successive measurement or sampling moments. Preferably, each value of the second signal S2 for a given measurement or sampling moment is determined as a sliding average of the last values of the high envelope, for example the last twelve values of the high envelope.

Figure 18:
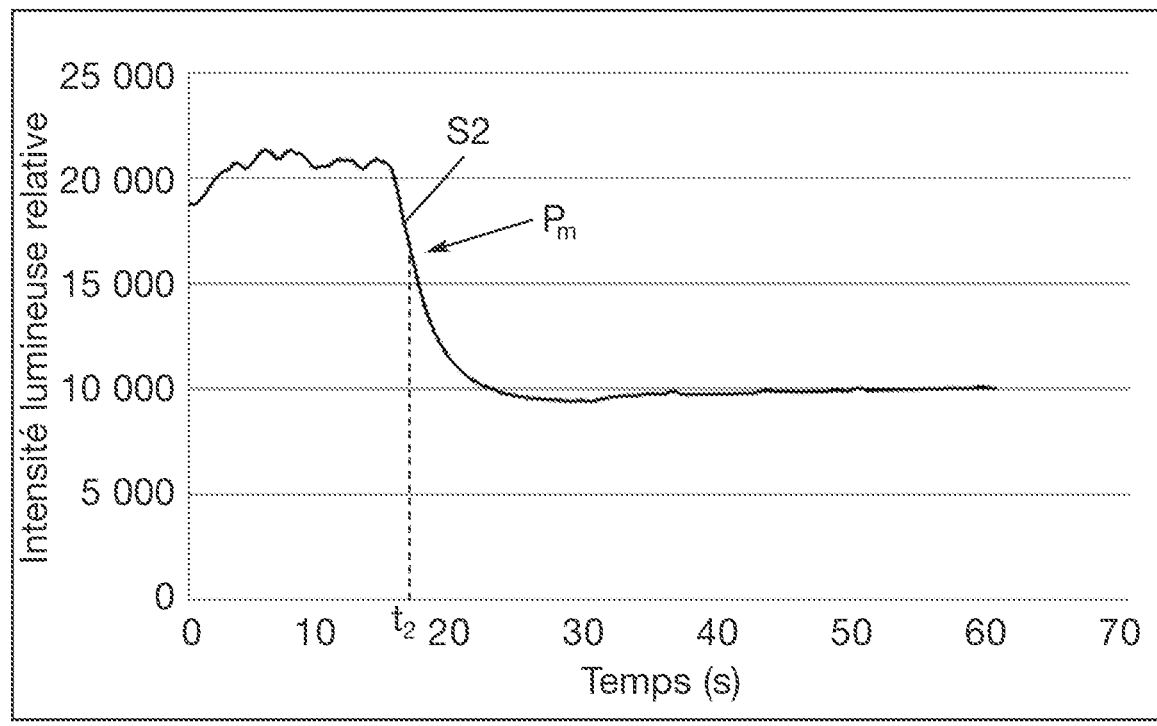
FIG. 18 is a diagram representing the evolution of the amplitude of an averaged high envelope of the measurement signal depending on the time.

FIG. 18 represents the evolution of the amplitude of the averaged high envelope depending on the time, and more particularly the evolution of the relative light intensity of the averaged high envelope depending on the time.

According to an embodiment of the invention, the processing unit 39 is configured to determine the maximum slope Pm of the second signal S2, the second value t2 of the coagulation time of the blood sample to be analyzed determined by the processing unit 39 then being the moment corresponding to said maximum slope.

According to an embodiment of the invention, the determination device 31 comprises an optical lens 41 disposed on the path of the incident light beam and configured to collimate the incident light beam 36.

The determination device 31 further comprises a loading system 42 configured to load and unload reaction cuvettes 2 into and out of the reaction housing. The loading system 42 advantageously includes a linear actuator, which may for example include an electric motor 43, such as an electric stepper motor.

Advantageously, the determination device 31 further comprises first and second members or bodies 44a, 44b respectively delimiting first and second housing portions 32a, 32b. The first and second members 44a, 44b are movably mounted relative to one another between a loading or unloading position (see FIG. 5) in which the first and second members 44a, 44b are spaced from one another and authorize a displacement of the reaction cuvette 2 until facing the first and second housing portions 32a, 32b, and a measurement position in which the first and second members 44a, 44b are brought closer to one another and delimit the receiving housing 32.

A method for determining the coagulation time of a blood sample to be analyzed using the determination device 31 will now be described.

Such a determination method comprises the following steps consisting in:
  providing a reaction cuvette 2 containing the blood sample to be analyzed 33,
  placing a ferromagnetic ball 11 on the raceway 9 of the reaction cuvette 2,
  placing the reaction cuvette 2 in the receiving housing 32 of the determination device 31,
  generating a magnetic field using the magnetic field generation system 34 so as to displace the ferromagnetic ball 11 along the raceway 9 in an oscillatory movement, the magnetic field being generated by sequentially supplying the coils of the two electromagnets 34a, 34b one after another,
  emitting an incident light beam 35 towards the blood sample to be analyzed 33 using the emission member 36,
  detecting, for example every 20 ms, a light beam 38 transmitted through the reaction cuvette 2 and coming from the incident light beam 36 using the detection member 37 so as to provide a measurement signal $S_M$,
  carrying out a first processing of the measurement signal $S_M$ using the processing unit 39 so as to provide a first signal S1 representative of the variation in particular of the amplitude of the movement of the ferromagnetic ball 11,
  carrying out a second processing of the measurement signal $S_M$ using the processing unit 39 so as to provide a second signal S2 representative of the variation in particular of the absorbance of the blood sample to be analyzed 33,
  determining, using the processing unit 39, a first value t1 of the coagulation time of the blood sample to be analyzed from the first signal S1,
  determining using the processing unit 39 a second value t2 of the coagulation time of the blood sample to be analyzed from the second signal S2, and
  comparing the first and second determined values t1, t2 of the coagulation time.

According to an embodiment of the determination method, the latter further comprises a step consisting in adjusting, and more precisely servo-controlling, the light intensity of the incident light beam 36 depending on an initial value of the measurement signal $S_M$ corresponding to a position of the ferromagnetic ball 11 substantially at the lowest point of the raceway 9. These arrangements allow servo-controlling the light intensity of the incident light beam 36 on the initial absorbance of the blood sample to be analyzed, and for example increasing said light intensity if the blood sample to be analyzed is initially very absorbent, or conversely, in particular in order to have the highest possible reference signal, without the risk of saturation.

According to an embodiment of the determination method, the latter further comprises a step consisting in adjusting, and more precisely servo-controlling, during an initial phase of the determination method, for example in the range of 1 to 2 seconds from the triggering of the movement of the ferromagnetic ball, at least one parameter representative of the magnetic field to which the ferromagnetic ball 11 is subjected depending on the initial values of the measurement signal $S_M$, and more particularly depending on the initial values of the first signal S1. The at least one parameter representative of the magnetic field may for example be the period and/or the intensity of the magnetic field generated by the magnetic field generation system 34. These arrangements allow optimizing the oscillation of the ferromagnetic ball 11 depending on the initial viscosity of the blood sample to be analyzed 33, and thus, for example, avoiding shocks of the ferromagnetic ball 11 against the walls of the reaction cuvette 2 or, conversely, avoiding the maximum amplitude of the ferromagnetic ball 11 being insufficient.

Figure 14:
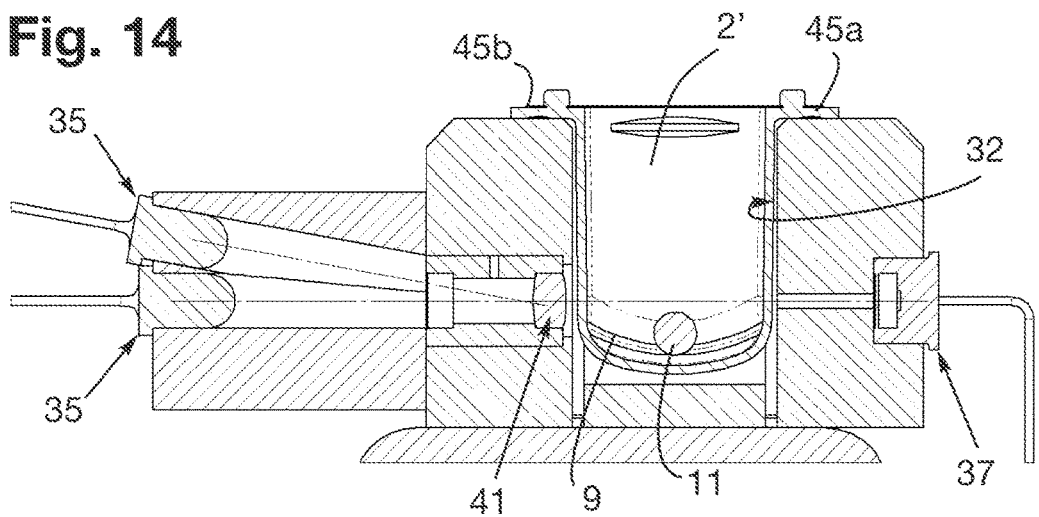

FIG. 14 represents a determination device 31 according to a second embodiment of the invention which differs from that represented in FIGS. 5 to 13 essentially in that the loading system 42 and the receiving housing 2 are adapted respectively for loading and receiving a set or block comprising a plurality of reaction cuvettes 2' connected to each other. The different reaction cuvettes 2' of such a set or block are for example molded in one piece from a plastic material. The reaction cuvettes 2' are advantageously adjacently disposed such that their longitudinal walls are parallel to each other. The reaction cuvettes 2' are for example connected at their upper portion by lateral connecting portions 45a, 45b.

As is evident per se, the invention is not limited to the sole embodiments of this determination device and this reaction cuvette, described hereinabove as examples, but it comprises on the contrary all variants thereof.

The invention claimed is:

1. A method for determining the coagulation time of a blood sample to be analyzed, comprising the following steps:
  providing a reaction cuvette containing the blood sample to be analyzed, the reaction cuvette comprising a bottom delimiting a concave raceway whose concavity is directed upwards;
  placing a ferromagnetic ball on the raceway of the reaction cuvette;
  subjecting the ferromagnetic ball to a magnetic field so as to displace the ferromagnetic ball along the raceway in an oscillatory movement;

exposing the blood sample to be analyzed to an incident light beam configured to be at least partially obscured by the ferromagnetic ball during at least one part of the oscillatory movement of the ferromagnetic ball along the raceway;

detecting at least one light beam transmitted through the reaction cuvette and coming from the incident light beam so as to provide a measurement signal;

carrying out a first processing of the measurement signal so as to provide a first signal representative of the variation of at least one physical quantity representative of the movement of the ferromagnetic ball;

carrying out a second processing of the measurement signal so as to provide a second signal representative of the variation of at least one optical property of the blood sample to be analyzed;

determining a first value of the coagulation time of the blood sample to be analyzed from the first signal; and determining a second value of the coagulation time of the blood sample to be analyzed from the second signal.

2. The determination method according to claim 1, wherein the first processing of the measurement signal is carried out such that the provided first signal corresponds to the deviation between a high envelope and a low envelope of the measurement signal.

3. The determination method according to claim 2, wherein the step for determining the first value of the coagulation time of the blood sample to be analyzed comprises a step consisting in providing a base signal corresponding to a sliding average of the first signal, the first value of the coagulation time of the blood sample to be analyzed being determined from the base signal.

4. A determination method according to claim 2, wherein the second processing of the measurement signal is carried out such that the provided second signal corresponds to a sliding average of the high envelope of the measurement signal.

5. The determination method according to claim 4, wherein the step for determining the second value of the coagulation time of the blood sample to be analyzed comprises a step consisting in determining the maximum slope of the second signal, the second value of the coagulation time of the blood sample to be analyzed being the moment corresponding to said maximum slope.

6. The determination method according to claim 1, wherein the step for determining the first value of the coagulation time of the blood sample to be analyzed comprises a step consisting in providing a base signal corresponding to a sliding average of the first signal, the first value of the coagulation time of the blood sample to be analyzed being determined from the base signal.

7. A determination method according to claim 6, wherein the second processing of the measurement signal is carried out such that the provided second signal corresponds to a sliding average of the high envelope of the measurement signal.

8. The determination method according to claim 7, wherein the step for determining the second value of the coagulation time of the blood sample to be analyzed comprises a step consisting in determining the maximum slope of the second signal, the second value of the coagulation time of the blood sample to be analyzed being the moment corresponding to said maximum slope.

9. The determination method according to claim 8, which comprises a step consisting in comparing the first and second determined values of the coagulation time.

10. The determination method according to claim 9, which further comprises a step consisting in adjusting the light intensity of the incident light beam depending on an initial value of the measurement signal.

11. The determination method according to claim 10, which further comprises a step consisting in adjusting, during an initial phase of the determination method, at least one parameter representative of the magnetic field to which the ferromagnetic ball is subjected depending on the initial values of the measurement signal.

12. A determination method according to claim 1, wherein the second processing of the measurement signal is carried out such that the provided second signal corresponds to a sliding average of the high envelope of the measurement signal.

13. The determination method according to claim 12, wherein the step for determining the second value of the coagulation time of the blood sample to be analyzed comprises a step consisting in determining the maximum slope of the second signal, the second value of the coagulation time of the blood sample to be analyzed being the moment corresponding to said maximum slope.

14. The determination method according to claim 1, which comprises a step consisting in comparing the first and second determined values of the coagulation time.

15. The determination method according to claim 1, which further comprises a step consisting in adjusting the light intensity of the incident light beam depending on an initial value of the measurement signal.

16. The determination method according to claim 1, which further comprises a step consisting in adjusting, during an initial phase of the determination method, at least one parameter representative of the magnetic field to which the ferromagnetic ball is subjected depending on the initial values of the measurement signal.

17. The determination method according to claim 1, comprising the following step:
providing a determining device comprising:
  a receiving housing in which the reaction cuvette containing the blood sample to be analyzed and the ferromagnetic ball is intended to be received;
  a magnetic field generation system configured to generate the magnetic field capable of displacing the ferromagnetic ball along the raceway in an oscillatory movement when the reaction cuvette is received in the receiving housing;
  an emission member configured to emit the incident light beam in the direction of the blood sample to be analyzed when the reaction cuvette is received in the receiving housing;
  a detection member configured to detect the at least one light beam transmitted through the reaction cuvette and coming from the incident light beam and to output the measurement signal; and
  a processing unit configured:
    to carry out the first processing of the measurement signal ($S_M$) so as to provide the first signal;
    to carry out the second processing of the measurement signal ($S_M$) so as to provide the second signal;
    to determine the first value of the coagulation time of the blood sample to be analyzed from the first signal; and
    to determine the second value of the coagulation time of the blood sample to be analyzed from the second signal.

18. The determination method according to claim 17, wherein the magnetic field generation system is transversely shifted relative to the general direction of extension of the raceway.

19. The determination method according to claim 17, wherein the determining device is configured such that, when the reaction cuvette is received in the receiving housing and the ferromagnetic ball is located at the lowest point of the raceway, the ferromagnetic ball partially obscures the incident light beam.

20. A reaction cuvette adapted for the implementation of the method according to claim 1, the reaction cuvette comprising:
   a receptacle configured to contain a biological fluid to be analyzed, the receptacle comprising:
   a lower portion including a bottom delimiting a concave raceway whose concavity is directed upwards, the raceway having the lowest point thereof substantially at its center and being intended to guide an oscillatory movement of a ferromagnetic ball;
   an upper portion delimiting an insertion opening;
   first hooking means configured to hook the reaction cuvette to a first adjacent reaction cuvette in a first hooking direction; and
   second hooking means configured to hook the reaction cuvette to a second adjacent reaction cuvette in a second hooking direction which is substantially perpendicular to the first hooking direction; and
   wherein the width of the lower portion of the receptacle transversely to the general direction of extension of the raceway is smaller than the width of the upper portion of the receptacle transversely to the direction of extension of the raceway, and the raceway is transversely shifted relative to a median longitudinal plane of the upper portion of the receptacle.

* * * * *